US005561520A

United States Patent [19]

Williams

[11] Patent Number: 5,561,520
[45] Date of Patent: Oct. 1, 1996

[54] MEASURING PROPERTIES OF A SLURRY

[75] Inventor: Richard A. Williams, Cornwall, United Kingdom

[73] Assignee: British Nuclear Fuels plc, Warrington, United Kingdom

[21] Appl. No.: 325,273

[22] PCT Filed: Feb. 28, 1994

[86] PCT No.: PCT/GB94/00390

§ 371 Date: Oct. 24, 1994

§ 102(e) Date: Oct. 24, 1994

[87] PCT Pub. No.: WO94/19674

PCT Pub. Date: Sep. 1, 1994

[30] Foreign Application Priority Data

Feb. 26, 1993 [GB] United Kingdom .................. 9303888

[51] Int. Cl.$^6$ .................................................. G01N 15/02
[52] U.S. Cl. ........................... 356/335; 73/61.71; 356/36
[58] Field of Search ................................. 356/335, 336, 356/36; 73/61.71, 61.73

[56] References Cited

U.S. PATENT DOCUMENTS 5,135,662  8/1992  Ho ............................................ 210/709

Primary Examiner—Richard A. Rosenberger
Attorney, Agent, or Firm—Nixon & Vanderhye P.C.

[57] ABSTRACT

An apparatus for measuring properties of a slurry which comprises a slurry transporting section (16), means for measuring (14a) at a first inspection site the particle size distribution of a slurry entering the transporting section, means for measuring (14b) at a second inspection site the particle size distribution of slurry leaving the transporting section and means for calculating (13a, 13b) from the particle size distribution measured at the first and second inspection sites a parameter related to the floc strength of the slurry which has passed between the first and second inspection sites.

The transporting section may comprise a pipe which includes a flow constriction.

The transporting section may be a removable section fitted between a slurry inlet means and an outlet means.

The said means for calculating may calculate one or more regression coefficients which define the curve described by the floc mass size equation or the breakage ratio define by the mean floc sizes before and after breakage. The means for measuring particle size at each inspection may comprise a scanning laser microscope.

11 Claims, 6 Drawing Sheets

MEASURING PROPERTIES OF A SLURRY

BACKGROUND OF THE INVENTION

1. Field of the Invention

The present invention relates to apparatus and a method for measuring one or more properties, especially related to floc strength, of a slurry.

2. Discussion of Prior Art

The lack of appropriate on-line and in-situ instrumentation for monitoring the size distribution of particulate matter in concentrated particulate (e.g. mineral) slurries has been a long standing and limiting constraint in the modelling and control of processing plants. Numerous on-line sizing instruments are available from commercial suppliers but, with few exceptions, these require sampling and/or dilution of the slurry prior to analysis. Such instruments utilise a variety of individual or hybrid sensing principles including ultrasonics, laser-diffraction, x-ray absorption and electrical properties. Alternative approaches have been suggested, such as centrifugal differentiation of particles according to their size in a spiral tube and detection of the resulting solids concentration variation across the tube using penetrating radiation. However, in all of these known categories of instrumentation the particulates are analysed in an environment that bears little resemblance to that encountered within the process stream or vessel to be used in a practical working system. Indeed, the solids concentration and the shear conditions often differ by several orders of magnitude, Consequently, the interpretation of results derived from such measuring devices has to be undertaken with some care, especially if the particulates are fine (<50 µm) and prone to aggregation.

SUMMARY OF THE INVENTION

According to the present invention in a first aspect there is provided an apparatus for measuring properties of a slurry which comprises a slurry transporting section, means for measuring at a first inspection site the particle size distribution of a slurry entering the transporting section, means for measuring at a second inspection site the particle size distribution of slurry leaving the transporting section and means for calculating from the particle size distribution measured at the first and second inspection sites a parameter related to the floc strength of the slurry which has passed between the first and second inspection sites.

According to the present invention in a second aspect there is provided a method of measuring one or more properties of a slurry using the apparatus of the first aspect which comprises introducing a slurry to be investigated to the said first inspection site, measuring the particle size distribution at the first inspection site, passing the slurry through the transporting section, measuring the particle size distribution at the second inspection site and calculating from signals representing the said particle size distributions a parameter related to the floc strength of the slurry.

The transporting section may comprise a pipe which may optionally include a flow constriction. Desirably, the transporting section is a removable section fitted between a slurry inlet means, e.g. an inlet reservoir, and an outlet means, e.g. an outlet reservoir. Desirably, different transporting sections, e.g. having different internal diameters and lengths and containing different flow constrictions (such as diameter reducing orifices or in-line mixer elements) may be fitted between the same positions between the inlet means and outlet means.

The said parameter which is calculated may be calculated using one of two methods.

In the first method one or more of the regression coefficients which for a given set of flow conditions define the solution to the floc mass size equation, Equation 1 given below are obtained. The regression coefficients K, $\alpha$, $\mu_f$ and $\sigma_f$, which are explained further below, can be calculated by fitting experimental particle size distribution data to an analytical solution of Equation 1. Thus, the regression coefficients describe the floc breakage under the shear conditions within the transporting section.

In the second method, a breakage ratio Br can be obtained, as defined in Equation 13—specified hereinafter. It is based on measurement of the average size by weight (or volume).

The first said method can be used to describe the behaviour of flocculated systems that once broken are unlikely to reform spontaneously (e.g. flocs that have been formed upstream of the breakage environment by polymer bridging and that are subsequently broken in a slurry where there is no excess polymer). The second said method can be used to describe any type of flocculation process whatever the mechanism of floc formation and reversibility. Thus, the breakage ratio can be used to describe floc breakage under shear conditions within the transporting section.

We have found by study of the behaviour of flocs in different floc transport environments that the mean floc size for a given sample is dependent on the root mean square velocity gradient G. The fundamental constant G characterises the hydrodynamic flow conditions and also the shear to which the floc is subjected.

If particle size distribution measurements are made by the method according to the second aspect of the present invention at various values of root mean square velocity gradient G and the values of the breakage ratio Br and regression coefficients K, $\alpha$, $\mu_f$ and $\sigma_f$ are calculated for each value of G and are plotted against G the plots will characterise the material under investigation. From such plots the behaviour of the material can be predicted under different conditions of use, e.g. in an industrial floc processing plant, provided the root mean square velocity gradient G can be evaluated for such conditions of use.

For flow of a floc through a pipe the floc root mean square velocity gradient G can be expressed simply by the well known relationship:

$$G = \sqrt{\frac{\Delta P}{\mu t}} \quad \text{(Equation 2)}$$

where $\Delta P$ is the pressure difference between the ends of the pipe, $\mu$ is the fluid viscosity and t is the time taken for transit of the floc from one end of the pipe to the other. Thus, in the method according to the second aspect of the present invention, the various values of root mean square velocity gradient G at which various particle size distribution measurements are carried out can be obtained by measurement of $\Delta P$, $\mu$ and t. The pressure difference $\Delta P$ can be estimated by measuring the floc pressure by pressure transducers at the respective ends of the said slurry transporting section and calculating the difference in the measured pressure values. The mean residence time t can be calculated knowing the volumetric slurry flow rate and volume of the transporting section. The viscosity of the floc material may be measured in a known manner, e.g. by the technique described in Applicants' GB 2233461.

Where plots of the aforementioned regression coefficients and breakage ratio against root mean square velocity gradient G for a given material have been made to characterise the material and the behaviour in another working environment which comprises a pipe is required to be predicted the velocity gradient G in the working environment needs to be known and can be measured in the above manner. Where the behaviour in a stirred tank is required to be predicted the root mean square velocity gradient G can be found using the relationship:

$$G = \sqrt{\frac{W}{\mu V}} \quad \text{(Equation 3)}$$

by measurement of W, μ and V where W is the stirrer input power, μ is the fluid viscosity and V is the volume of fluid in the tank.

In order to produce different flow conditions using the apparatus according to the first aspect of the present invention the apparatus may comprise means for varying and controlling the volumetric flow rate of slurry entering the transporting section, e.g. by using a controlled variable flow rate pump, or by application of various different known pressure drops, e.g. by pressurising the inlet means (e.g. inlet reservoir) or applying suction to the outlet means (e.g. outlet reservoir). Alternatively, or in addition, the regression coefficients may be computed and the value of G measured with changes in the transporting section as described above.

Where the flow rate of the floc is varied this may be varied according to a known flow rate function, e.g. a flow rate which increases linearly with time in a ramped fashion, the various values of G being measured for corresponding points on the flow rate function.

The means for measuring the particle size distribution at the first inspection site and the means for measuring the particle size distribution at the second inspection site may each comprise a scanning laser microscope. Such devices, which are known per se, may comprise means for scanning a laser beam over a given particle and means for measuring by inspecting back-scatter of the laser beam, the time taken for the beam to travel along the given particle. In known instruments operating in this way the laser beam is focused to a very tiny beam spot, typically 2×0.8 μm with a smaller dimension in the scanning direction to give maximum illumination. The particles measured can for example be in the size range 1 μm to 1 mm.

The detected pulses produced by back-scattered light from individual particles going through the focal point of the laser beam represent the measurement of individual particles. In this sense the device can be considered to be a particle number counting device, which is ideal for use in providing information for population balance purposes. The laser beam is scanned at a fixed velocity and the time taken for the beam to scan across a given particle is a direct measure of the size of that particle. The size distribution is computed from the statistical distribution of random chord lengths through a population of, for example, spheres in a known way. The laser beam is desirably scanned very rapidly to make the measurement less sensitive to any change in flow conditions.

The apparatus according to the present invention may further include means for measuring the particle size distribution at a third inspection site in the inlet means, e.g. inlet reservoir.

Measurements can be performed using the apparatus and method of the present invention using different electrolytes (e.g. differing in pH, ionic strength, in presence of different surfactants) to probe the effects of interparticle forces on floc strength. The effect of floc shape on floc strength can also be evaluated. Size analysis can also be performed in the inlet reservoir at the third inspection site e.g. to investigate different aggregation protocols (mixing rates, flocculant dosage etc). Hence the flocs entering the transporting section for testing can be fully characterised.

The invention provides means for carrying out a series of rapid standard tests to assess the likely behaviour of a given flocculated system under realistic process hydrodynamic conditions. Hence the effect of preparing flocculated feedstocks using different preparation methods (chemical addition rates etc) can be optimised by use of the invention. This allows rapid screening of operating conditions to be encountered in an industrial processing plant.

The present invention also allows elucidation of floc breakage mechanisms in a given floc. For instance, floc breakage occurring through "erosion" processes produces a dramatic increase in the number count rate, whereas "rupture" dominated breakage reduces average size markedly but does not increase number count so greatly.

The present invention allows wholly on-line particle size analysis of a slurry to be carried out without the need for ex-situ sampling of a stream of the slurry. Automated control allows floc breakage characteristics to be measured quickly over a wide range of selectable controlled flow conditions. The invention therefore allows optimisation of floc formulation and prediction of how flocs will behave during industrial transport and processing, e.g. pipelines and separators.

BRIEF DESCRIPTION OF THE DRAWINGS

Embodiments of the present invention will now be described by way of example with reference to the accompanying drawings, in which.

DETAILED DESCRIPTION OF PREFERRED EMBODIMENTS

Figure 1:
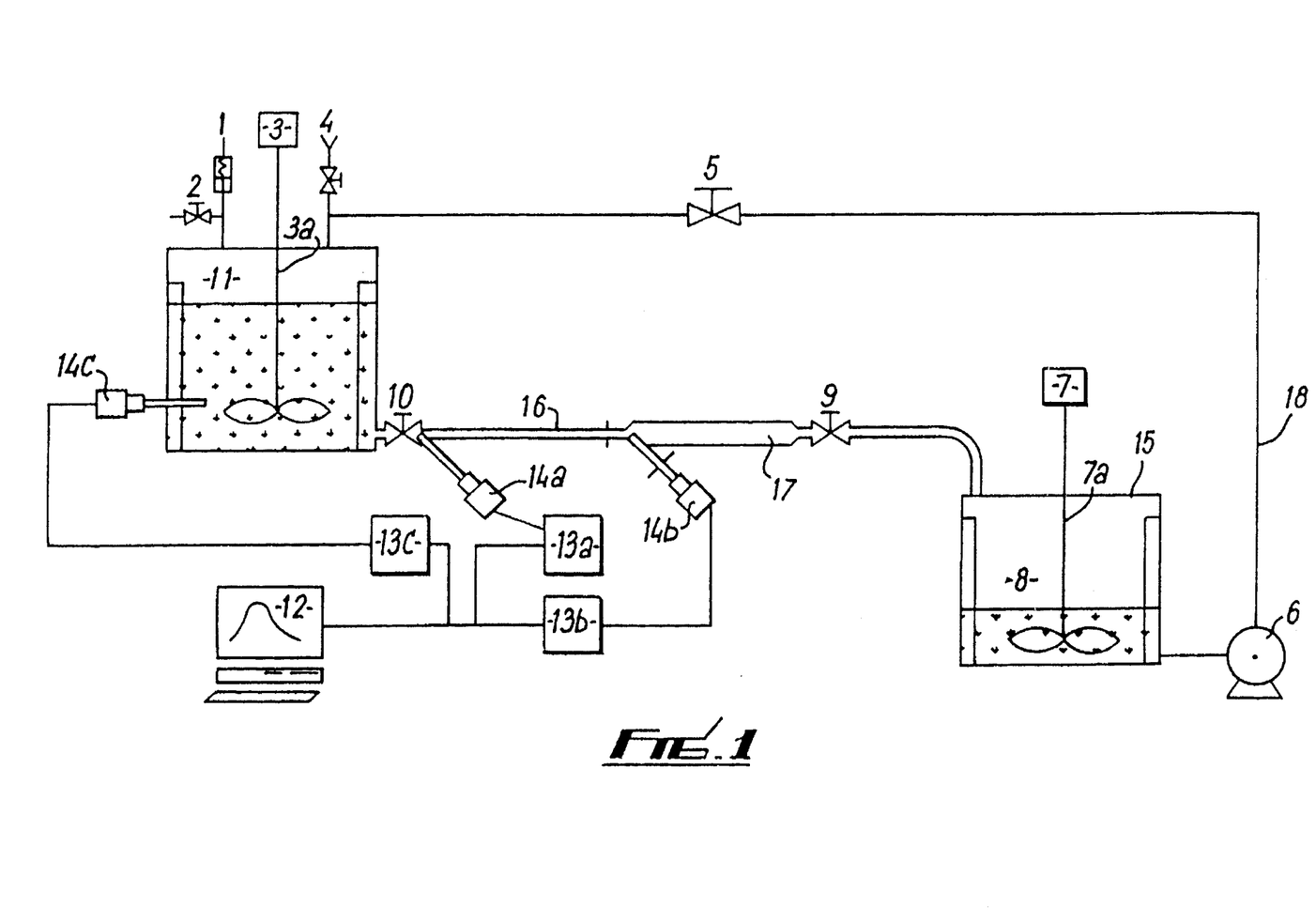
FIG. 1 is a partly schematic side view of a floc analysis apparatus.

As shown in FIG. 1, a slurry of aggregated particles, e.g. produced using flocculants is prepared and introduced to an inlet reservoir 11 via an inlet 4. The contents of the reservoir 11 may be gently agitated by a stirrer 3a operated by an adjustable speed motor 3. The reservoir 11 may be pressurised by the introduction of air through an air inlet 2 having a pressure relief mechanism 1. The slurry is passed via a ball valve 10 through a constricted pipe comprising a measurement section 16.

The slurry in the inlet reservoir 11 is inspected by a scanning laser microscope probe 14c. The slurry entering the measurement section 16 is inspected by another scanning laser microscope probe 14a and the slurry leaving the measurement section 16 is inspected by a further scanning laser microscope probe 14b. Slurry leaving the measurement section 16 is conveyed by a further pipe 17 having a flow rate control valve 9 to an outlet reservoir 8 having a stirrer 7a controlled by a stirrer motor 7 and an outlet air line 15 to a vacuum pump (not shown).

If required, for measurements of flocs during operation in closed-circuit continuous flow, slurry from the outlet reservoir 8 may be returned to the inlet reservoir 11 via a return pipe 18 having a valve 5 the return being effected by a pump 6. The returned slurry is re-introduced into the inlet reservoir 11 via the inlet 4.

The electrical outputs of the probes 14a, 14b and 14c are supplied respectively to processing units 13a, 13b and 13c the output of which units are fed separately to a computer 12.

The flow rate of slurry passing through the measurement section 16 may be controlled by applying pressure in the inlet reservoir 11 and/or by applying vacuum to the outlet reservoir 8 and/or by adjusting the valve 9. In the latter case valve 10 may be omitted. These adjustments may be carried out by computer control e.g. using a control signal from the computer 12 to operate the relevant valves via known electromechanical actuator devices.

Figure 2:
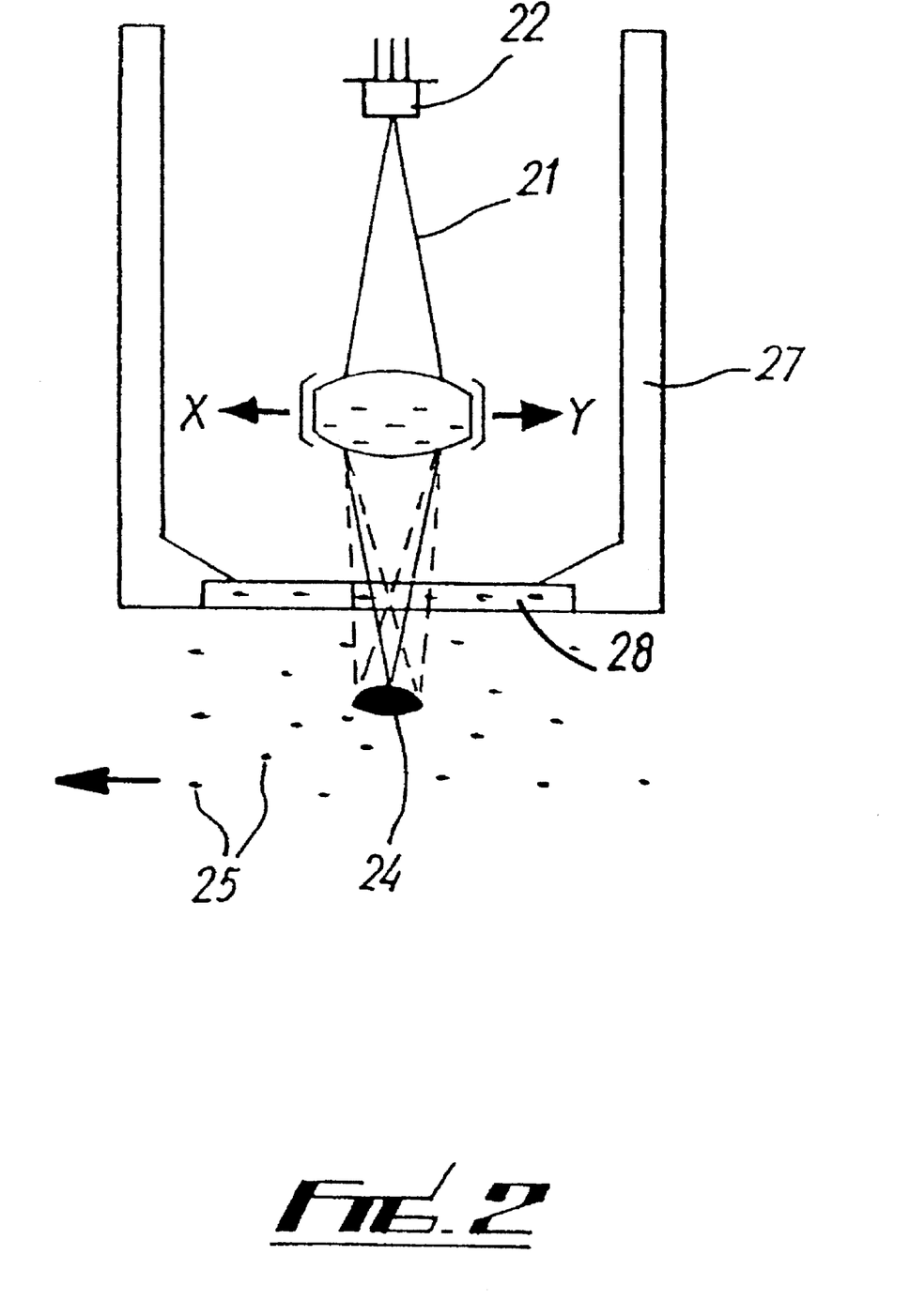
FIG. 2 is a cross-sectional side view (not to scale) of the scanning laser microscope probe used in the apparatus of FIG. 1 in use.

The probes 14a, 14b and 14c each operate as shown in FIG. 2. A laser beam 21 generated by a dual source/detector unit 22 housed inside a probe head 27 is focused through a window 28 in the head 37 by a lens 33 to form a high intensity beam spot 24 in the slurry represented by particles 25. In the case of the probes 14a and 14b the slurry is flowing in a direction X in the measurement section 16. The lens 23 is scanned in the direction X and also the reverse direction Y by the lens 23 whereby the beam spot 24 traces an ellipse in the flow of the particles 25.

The scanning laser microscope probes 14a, 14b and 14c may be commercially available devices supplied by Lasentec Corporation, USA (type PAR-TEC 100, 200 or 300).

The pulses produced at the unit 22 by back-scattered light from individual particles 25 going through the spot 24 represent the measurement of those individual particles. As the particle size is determined by the detected signal time (pulse width) rather than by the intensity of the detected pulse (pulse amplitude), the measurement is less influenced by the colour and reflectivity of the particles or the absorption coefficient of the suspending fluid.

The output of the unit 22 is fed to the processor 13 (13a, 13b or 13c as appropriate) which records the entire particle size range of 1–1000 µm in 38 separate size channels, using eight registers to accumulate particle "counts" in each channel over precise time periods (0.2–3.2 s), as specified by the user. At the end of the eighth counting period the contents of the eight registers are transferred to the computer 12 and the number-size distribution may be statistically computed and displayed by the computer 12. The computer 12 also calculates and displays the breakage function from the sets of results representing size distributions obtained from the processors 13a, 13b for a given slurry flow.

In order to demonstrate use of the apparatus shown in FIGS. 1 and 2 the following slurry materials may be used.

Slurries of 1–5% by volume of a polydispersed silica may be prepared by mixing with tap water. The silica, Microsil ED (Trade Mark), Crosfield Chemicals, has a spherical equivalent mean size in the region of 40 µm with a range of 4–125 µm. To these slurries may be added either:

(a) a 'mixed' cationic flocculant prepared by blending a 0.05 wt % Zetag 92 (Trade Mark) solution and 0.5 wt % Magnafloc 1967 (Trade Mark) solution in a volume ratio of 1:1 (both supplied by Allied Colloids Ltd), or (b) a single flocculant Zetag 92 (0.05 wt % solution).

Zetag 92 is an ultra-high molecular weight polyacrylamide carrying a medium charge density, whilst Magnafloc 1967 is a low molecular weight specifies carrying a high charge. Flocculant dosages may be selected on the basis of preliminary tests which identify conditions that could produce given floc size distributions in a reproducible manner. The flocculation can be enhanced by using "mixed" flocculants, and these are suitable for use at the higher solids concentrations (5% v/v), otherwise large volumes of Zetag 92 are required to achieve a given dosage per unit surface area, with a consequent effect on the viscosity of the continuous phase. All experiments may be performed at room temperature (18°±2° C.).

Figure 3:
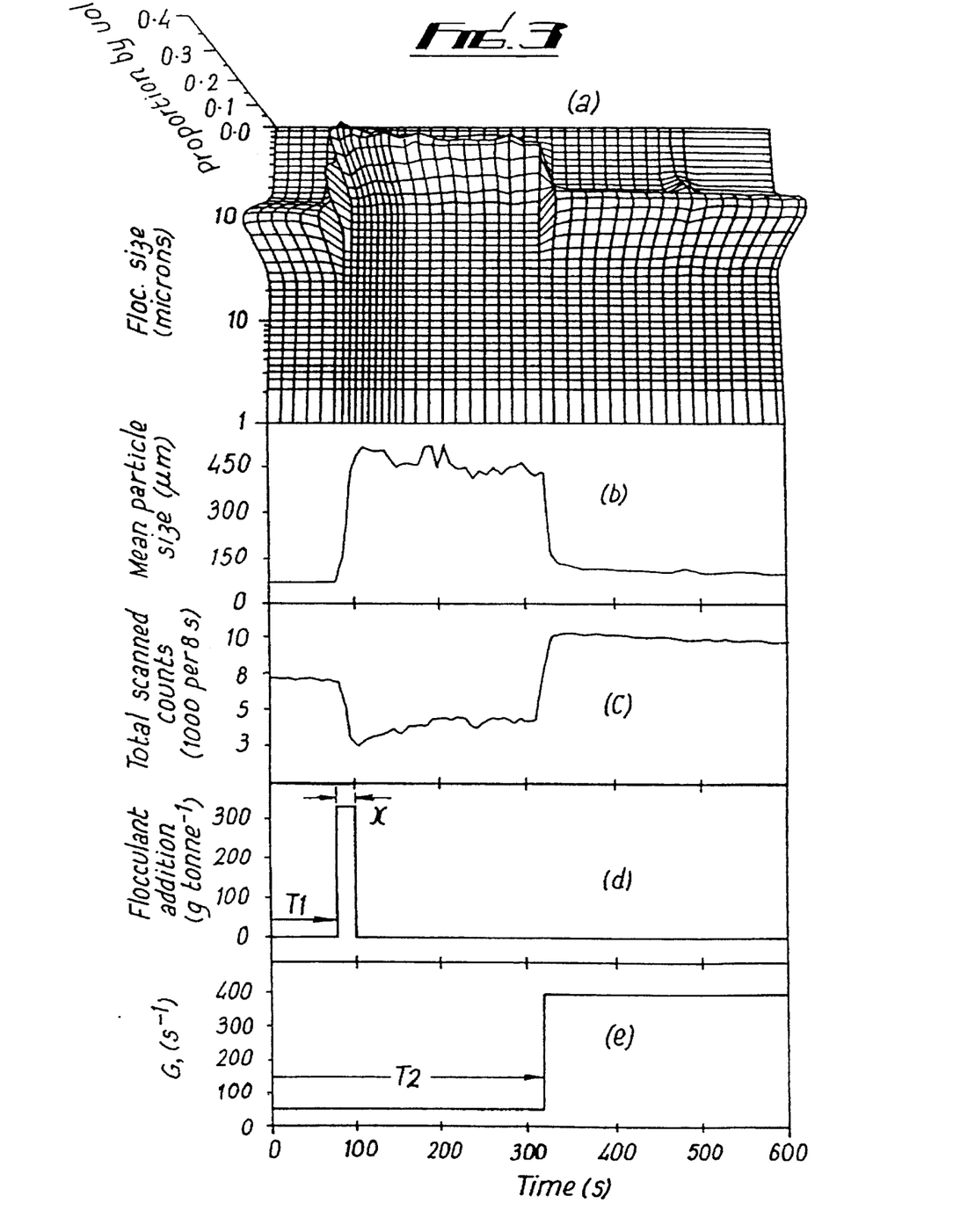
FIG. 3 is a graph of various parameters versus time for a floc in the inlet reservoir of the apparatus shown in FIG. 1.

FIG. 3 illustrates how the floc size per se may be investigated in the reservoir 11 by the probe 14c using silica flocs. Flocculant is added to the slurry in the reservoir 11 for a period x after a given time T1 as indicated in FIG. 3(d) and the stirring rate in the reservoir is increased from 50 s$^{-1}$ to 400 s$^{-1}$ after a given time T2 as indicated in FIG. 3(e). The mean floc size increases after time T1+x by addition of the flocculant as indicated in FIG. 3(b) and then decreases after time T2 (FIG. 3(b)) because of the increased stirring. The number of particles counted per unit volume decreases during the period x and then increases again after time T2 as indicated in FIG. 3(b). FIG. 3(a) shows the particle size distribution changing during these events.

Figure 4:
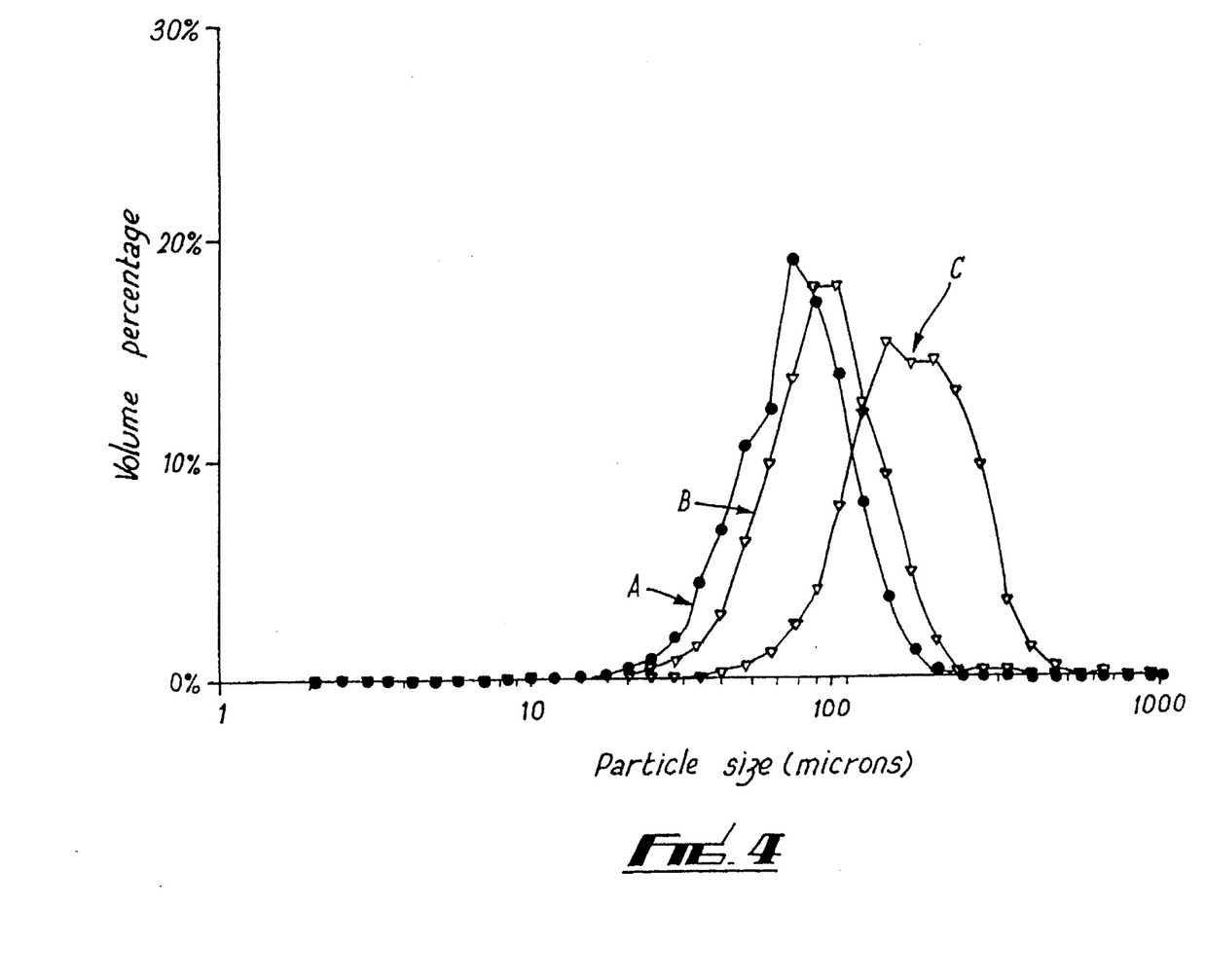
FIG. 4 is a graph of volume percentage of particles versus particle size for an example of a slurry measured using the apparatus shown in FIG. 1.

FIG. 4 shows the measured size distributions under different conditions for a given slurry material. Curve A shows the size distribution of the primary particles before flocculation measured in the reservoir 11 by the probe 14c. Curve B represents the size distribution after flocculation as measured by the probe 14a where the particles were flowing in a flow having a Reynolds number of 33,000. Curve C represents the size distribution after flocculation and after passing through the measurement section 16 (FIG. 1) as measured by the probe 14b, the Reynolds number here being 12,700 due to the constricted flow in the measurement section 16.

Figure 5:
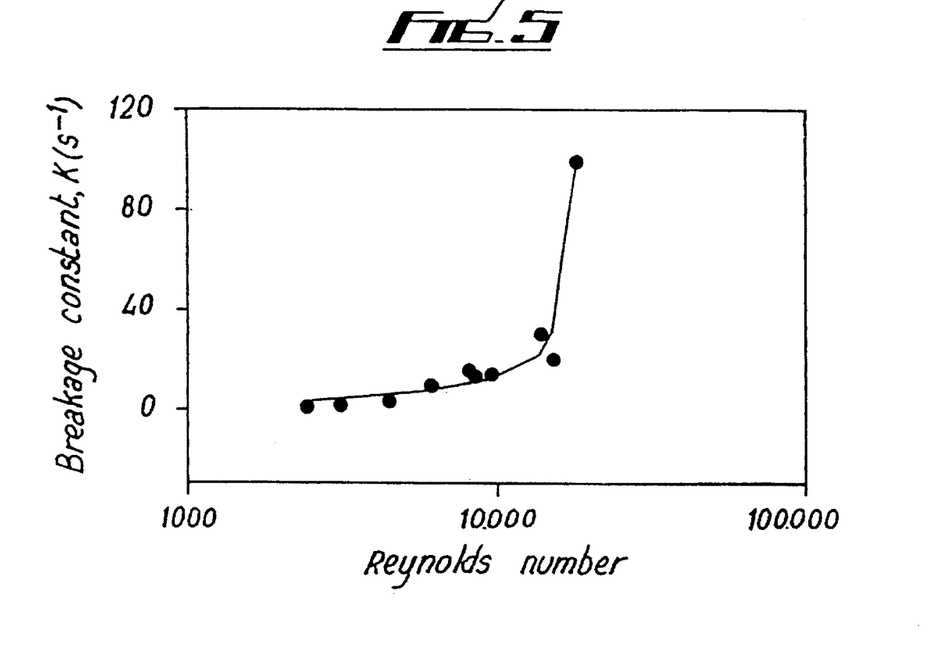
FIG. 5 is a graph of breakage constant versus Reynolds number for a given floc measured in the apparatus shown in FIG. 1.

FIG. 5 illustrates the results of a computation carried out by the computer 12 using two sets of particle size distribution results obtained from the probes 14a, 14b. As shown in FIG. 4 the breakage constant K explained below is measured as a function of Reynolds number. This procedure may be repeated for flocs that have been formed (in reservoir 11) using different reagents—hence optimal floc formation and handling characteristics may be deduced.

The following is our detailed analysis of the calculation procedure for coefficients of floc breakage in a breakage kinetics model.

If in a batch system it is assumed:

the flocculation process in the system has reached equilibrium after polymer addition;

the system is subjected to a step increase of agitation intensity;

no further polymer flocculant is added;

the floc breakage can then be assumed to be the dominant process. If the floc sizes in the system are divided into $N_{chn}$ classes from the largest to smallest according to the diameters, the mass-size balance equation caused by floc breakage for the ith class can be written as:

$$\frac{dM_i(t)}{dt} = b_{ij}S_jM_j(t) - S_iM_i(t) \qquad \text{Equation (1)}$$

in which:

$M_i(t)$ represents the mass fraction of flocs which lie in size class i at time t;

$S_i$ is the specific rate of breakage. If $S_j$ is the specific rate of breakage of material of size j and $M_j(t)$ is the mass fraction at time t of size j of the total mass w of particles in a batch test, then the rate of breakage of material of size j is $S_jM_j(t)W$;

$b_{ij}$ is the breakage distribution function. When material of size j breaks, it produces a suite of daughter particles. This suite, before rebreakage occurs, is called the primary progeny distribution, $B_{ij}$. This is the cumulative weight fraction of material broken from interval j which appears below size $X_i$, the upper size of interval i. The fraction of primary breakage products from interval j which goes into interval i is denoted by the symbol $b_{ij}$ and it may be calculated from:

$$b_{ij} = B_{ij} - B_{i+1,j} \qquad \text{(Equation 4)}$$

The first term on the right hand side of Equation (1) represents the birth rate of particles in size class i and the second one represents the death rate of particles in the size class.

The analytical solution to Equation 1 is:

$$M_i(t) = \sum_{j=1}^{i} h_{ij} e^{-S_j t} \qquad \text{(Equation 5)}$$

where $h_{ij} = 0$ for $i < j$ $h_{ij} = M_1(0) - \sum_{k=1}^{i-1} h_{ik}$ for $i = j$ $h_{ij} = \frac{1}{S_i - S_j} \sum_{k=j}^{i-1} S_K b_{ik} h_{kj}$ for $i > j$ If all values of $S_i$ and $b_{ij}$ are known, then the Equation 5 describes the floc size distribution at any time.

However theoretical functional forms for $S_i$ and $b_{ij}$ are not available. To overcome this an empirical form which has been accepted by most of the previous investigators in this field has been chosen for the specific rate of breakage:

$$S_i = K \left( \frac{X_i}{X_1} \right)^\alpha \qquad \text{(Equation 6)}$$

where K and α are constants dependent on specific experimental conditions, $X_1$ is the size of class 1.

Similar to the specific rate of breakage, various forms of breakage distribution function have been used by previous investigators, however, tremendous difficulties were found when using such functions. In order to reduce the number of unknown parameters and avoid the difficulty of the data fitting process, the primary breakage distribution is assumed to conform to the $S_B$ function of the log-normal distribution. The cumulative $S_B$ function of log-normal distribution is:

$$B_{ij} = \frac{1}{2} + \frac{1}{2} erf\left( \frac{Z}{\sqrt{2}} \right) \qquad \text{(Equation 7)}$$

where $$Z = \mu_J + \sigma_J \ln\left( \frac{X_i}{X_j - X_i} \right) \qquad \text{(Equation 8)}$$

and erf(Z) is the error function.

It is seen that if the coefficients K and α in Equation 6, and $\mu_J$ and $\sigma_J$ in Equation 8 are known, the mass fraction of each channel at any time t can be calculated by combining Equations 5, 6 and 7.

Therefore, if the size distribution of flocs in a batch system is measured directly as a function of time, then the mass fraction of each channel at any time can calculated assuming the floc density is constant. By fitting these data to the above model, the coefficients of K, α, $\mu_J$ and $\sigma_J$ can be obtained.

Employing the least squares fitting method (described below), Equation 1 can be solved for the constants K, α, μ, and σ, for the given experimental system using the apparatus described with reference to FIG. 1. These parameters provide a model which describes the floc breakage characteristics. Hence if $$f_i(K,\alpha,\mu_J,\sigma_J) = M_i^c(t_j) - M_i^m(t_j) \qquad \text{(Equation 9)}$$

where c value computed from the model m experimentally measured value l 1,2, . . . maximum number of particle size channels, Nchn j 1,2, . . . number of data points each channel for time sequence, Npts i 1,2, . . . Nchn×Npts the task is to minimise:

$$F(K,\alpha,\mu_J,\sigma_J) = \sum_{i=1}^{N_{chn} \times N_{pts}} [f_i(K,\alpha,\mu_J,\sigma_J)]^2 \qquad \text{(Equation 10)}$$

Satisfactory values of K, α, $\mu_J$, $\sigma_J$ are assumed to have been found when a minimum is reached in Equation 11. It should be noted that the experimental data can be smoothed using a log-normal density function before fitting to the model. Generally the smoothing procedure does not change the quality of fit of the results but significantly reduces the computation convergence time.

This approach can be used, for example, to measure breakage of flocs in a stirred tank (e.g. reservoir 11, FIG. 1) when the flocs are subjected to a change in rms velocity gradient.

Table 1 as follows lists the constants K, α, $\mu_J$, $\sigma_J$ as a function of nominal velocity gradient estimated by Equation 10 using the full size distribution data. In general it is found that the constants K and α, defining the specific rate of floc breakage, increase as the nominal velocity gradient G increases. However, the constants $\mu_J$ and $\sigma_J$, defining the primary distribution function, are not greatly influenced by changes in the nominal velocity gradient.

TABLE 1

Regression coefficients for experimental data: Effect of agitation intensity

| ΔG, (s⁻¹) | K (s⁻¹) | α | $\mu_J$ | $\sigma_J$ |
|---|---|---|---|---|
| 50 | 0.013 | 1.4 | 0.74 | 8.20 |
| 100 | 3.3 | 4.7 | 2.67 | 3.37 |
| 150 | 12.3 | 5.3 | 2.02 | 2.65 |
| 250 | 89.2 | 6.0 | 2.47 | 2.89 |

TABLE 1-continued

Regression coefficients for experimental data:
Effect of agitation intensity

| $\Delta G$, (s$^{-1}$) | K (s$^{-1}$) | $\alpha$ | $\mu_J$ | $\sigma_J$ |
|---|---|---|---|---|
| 300 | 3589 | 8.1 | 2.54 | 2.64 |
| 350 | 18061 | 8.5 | 2.87 | 3.14 |

Curves of $\Delta G$ v K, $\alpha$, $\mu_J$ and $\sigma_J$ plotted from Table 1 can be used to characterise the material under investigation.

Figure 6:
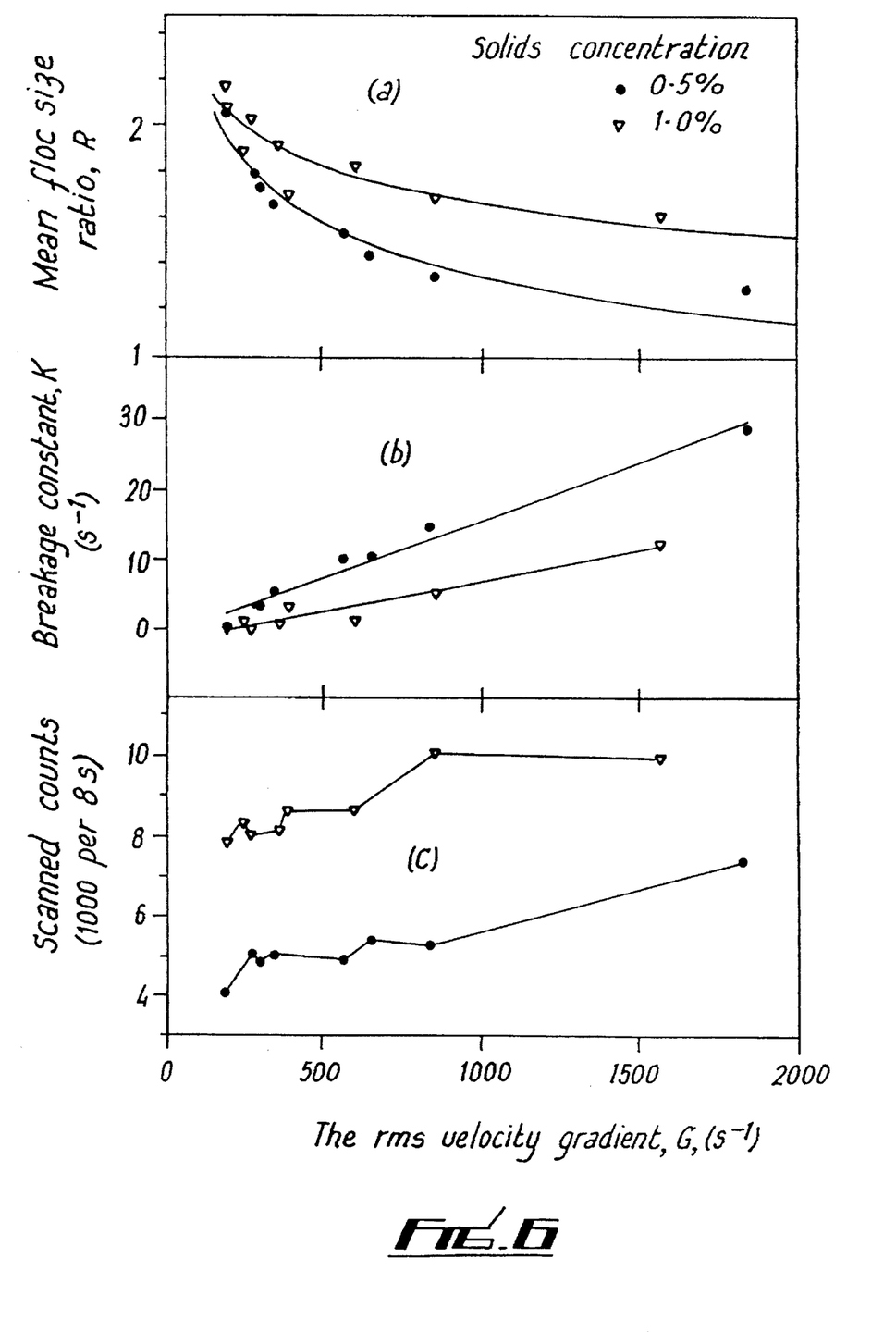
FIG. 6 is a graph of measured floc size (expressed in a dimensionless form, R, where R is the mean floc size leaving the transporting section normalised with respect to the initial floc size entering the transporting section) for different rms velocity gradients and the corresponding breakage parameter K, for two different slurry concentrations.

Equation 10 can be used to describe the overall global breakage process in the transportation pipe section (16, FIG. 1) in which case the number of data points in each size channel sequence ($N_{pts}$) is two. FIG. 6 shows an example of the breakage response of two polymer flocculated silica slurries at different solids concentrations. FIG. 6a shows the mean floc size R versus rms veolcity gradient. FIG. 6c shows the number of particles scanned by the size analyser. Thus practical and useful design correlations of R, K etc. vs. G can be obtained, e.g.

$$R=1+a.G^b \quad \text{(Equation 11)}$$

where a=34.69, b=0.67 (for 0.5% v/v slurry)

$$K=cG+d \quad \text{(Equation 12)}$$

where c=0.170, d=−0.88 (for 0.5% v/v slurry)

Using the second method for quantifying the breakage behaviour, the breakage ratio Br is given by Equation 13:

$$Br=(d_o-d_1)/(d_o-d_p) \quad \text{(Equation 13)}$$

where

Br is the breakage ratio $d_o$ is the mean initial floc diameter before breakage in the transporting section $d_1$ is the mean floc diameter in the process or transporting section after breakage caused by a change in the flow condition $d_p$ is the mean diameter of the original primary (unaggregated) particles.

Hence if Br tends to a value of unity at a given time or position the flocs are totally broken. If the floc size remains unchanged (unbroken) Br tends to zero. If aggregation (floc growth) occurs in the transporting section then Br is less than zero.

Figure 7:
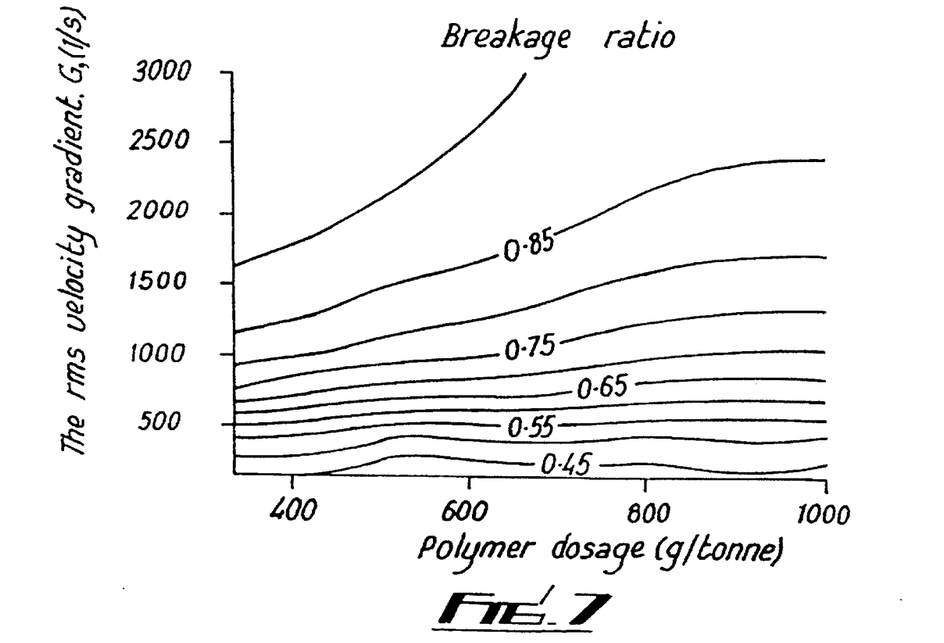
FIG. 7 is a graph of the breakage ratio Br versus the polymer dosage as function of the rms velocity gradient.

FIG. 7 shows the value of the breakage ratio as a function of polymer dosage for different rms velocity gradients in the transporting section. The dependence of Br on the nature of the floc and the hydrodynamic flow environment prevailing in the pipe is clearly evident. This provides a quantitive method for ranking flocculants, optimising their dosage and identifying inappropriate processing conditions which may cause unwanted degradation of the floc during hydraulic transport.

I claim:

1. An apparatus for measuring properties of a slurry which comprises:

a pipe;

means for feeding a slurry through said pipe;

means for varying the velocity gradient of the slurry along said pipe;

means for measuring at a first inspection site the particle size distribution of a slurry entering the pipe;

means for measuring at a second inspection site the particle size distribution of a slurry, said slurry at said second inspection site having a velocity different from a velocity of said slurry at said first inspection site; and means for calculating, from the particle size distribution measured at the first and second inspection sites, a parameter related to the floc strength of the slurry.

2. Apparatus as in claim 1 wherein the pipe includes a flow constriction.

3. Apparatus as in claim 1 wherein the pipe is a removable section fitted between a slurry inlet means and an outlet means.

4. Apparatus as in claim 1 wherein the means for calculating calculates at least one regression coefficient which defines a curve described by the floc mass size equation.

5. Apparatus as in claim 1 wherein the means for calculating calculates the breakage ratio defined by the mean floc sizes before and after breakage.

6. Apparatus as in claim 1 wherein the means for measuring the particle size distribution at the first inspection site and the means for measuring the particle size distribution at the second inspection site each comprise a scanning laser microscope.

7. Apparatus as in claim 6 wherein each scanning laser microscope is capable of producing a laser beam spot which may be scanned at a fixed velocity within the slurry whereby the time taken for the beam to scan across a given particle is a direct measure of the size of that particle.

8. Apparatus as in claim 1 which includes further means for measuring the slurry particle size distribution at a third inspection site in an inlet means.

9. A method of measuring at least one property of a slurry using the apparatus of claim 1, said method comprises:

introducing a slurry to be investigated to the first inspection site;

measuring the particle size distribution at the first inspection site;

passing the slurry through the pipe;

measuring the particle size distribution at the second inspection site; and calculating from signals representing the particle size distributions a parameter related to the floc strength of the slurry.

10. A method as in claim 9 wherein the calculating step includes the steps of:

calculating at least one regression coefficient which defines the curve described by the floc mass size equation of the slurry;

varying the velocity gradient of the slurry in the pipe;

measuring the different velocity gradients; and plotting said at least one of said regression coefficients against the velocity gradient to characterise the slurry material.

11. A method of measuring at least one property of a slurry, said method comprises:

introducing a slurry to be investigated at a first inspection site;

measuring the particle size distribution at the first inspection site;

passing the slurry through a pipe to a second inspection site;

measuring the particle size distribution at the second inspection site;

calculating from signals representing the measured particle size distributions a parameter related to the floc strength of the slurry, wherein the calculating step includes the steps of:

calculating at least one regression coefficient which defines the curve described by the floc mass size equation of the slurry;

varying the velocity gradient of the slurry in the pipe;

measuring the different velocity gradients; and plotting said at least one of said regression coefficients against the velocity gradient to characterise the slurry material.

* * * * *